US006586609B2

(12) United States Patent
Ruggieri et al.

(10) Patent No.: US 6,586,609 B2
(45) Date of Patent: Jul. 1, 2003

(54) PROCESS FOR ESTERIFICATION IN A CHROMATOGRAPHIC REACTOR

(75) Inventors: Roberto Ruggieri, Milan (IT); Giovanni Ranghino, Milan (IT); Gianni Carvoli, Novara (IT); Agostino Tricella, Bollate (IT); Davino Gelosa, Travaco' Siccomario (IT); Massimo Morbidelli, Milan (IT)

(73) Assignee: La Chemical SpA, Biella (IT)

( * ) Notice: Subject to any disclaimer, the term of this patent is extended or adjusted under 35 U.S.C. 154(b) by 0 days.

(21) Appl. No.: 09/999,494

(22) Filed: Nov. 30, 2001

(65) Prior Publication Data

US 2002/0082446 A1 Jun. 27, 2002

(30) Foreign Application Priority Data

Nov. 30, 2000 (EP) .............................. 00204266

(51) Int. Cl.[7] .......................... C11B 13/00; C11B 3/00; C11B 7/00; C07C 57/00; C07C 67/02
(52) U.S. Cl. ...................... 554/174; 554/227; 554/229; 560/61; 560/64; 560/103; 560/106; 560/109; 560/190; 560/193; 560/198; 560/231; 560/248; 560/263; 560/265
(58) Field of Search .................. 560/263, 265, 560/103, 106, 109, 190, 193, 198, 231, 248, 61, 64; 554/174, 227, 229

(56) References Cited

U.S. PATENT DOCUMENTS

| 4,435,595 A | 3/1984 | Agreda et al. .............. 560/234 |
| 5,405,992 A | 4/1995 | Funk .......................... 560/239 |
| 5,618,972 A | 4/1997 | Funk .......................... 560/265 |

OTHER PUBLICATIONS

The Hydrogen Bond. Pimentel and McClellan, Linus Pauling, editor, W.H. Freeman and Co. pp. 37–40 (1960).*
Organic Chemistry, 2$^{nd}$ Ed. McMurry, Brooks/Cole Publishing Co. pp. 171–722 (1988).*
Organic Chemistry, 5$^{th}$ Ed. Morrison and Boyd, Allyn and Bacon, Inc. pp. 636–639 (1987).*
Sardin, et al., "Esterification Catalysee par uyne resine exchangeuse de cation dans un reacteur chromatographique," *Noveau Journal de Chimie*, vol. 3, No. 4–1979, pp. 255–261.
Mazzotti, et al., "A Continuous Chromatographic Reactor: SMBR", Chem. Eng. Science, vol. 51, No. 10, 1827–1836, 1996.
Mazzotti, Marco, et al., *Kinetics, Catalysis, and Reaction Engineering*, "Kinetics of Liquid–Phase Esterification Catalyzed by Acidic Resins", Ind. Eng. Chem, Res. 1997, 36, 3–10.

* cited by examiner

*Primary Examiner*—Richard L. Raymond
*Assistant Examiner*—Zachary C. Tucker
(74) *Attorney, Agent, or Firm*—Perkins Coie LLP (57) ABSTRACT

Process for the esterification of organic acids with alcohols in a reactor of the chromatographic type in which the heterogeneous solid phase is capable of acting both as an esterification catalyst and as a means exhibiting preferential adsorption towards one of the reaction products (typically water). The process to which the present invention relates is particularly improved compared with conventional technology owing to the use, as the means for regenerating the catalyst, of a desorbent to which has been added a second compound, generally the anhydride of the acid used in the esterification reaction, which, by chemical reaction, completes the removal of the adsorbed water.

22 Claims, 7 Drawing Sheets

FIGURE 6 triacetin synthesis and desorption T=40°C Rmol gly/AcOH/Ac2O/H2O 1/.97/.07/0

FIGURE 7 Triacetin synthesis and desorption T=30°C Rmol gly/AcOH/Ac2O/H2O 1/0/0/0

PROCESS FOR ESTERIFICATION IN A CHROMATOGRAPHIC REACTOR

This application claims foreign priority under 35 U.S.C. §119 of EPO patent application 00204266, filed Nov. 30, 2000, incorporated herein by reference.

The present invention relates to a process for the esterification of organic acids with alcohols in a reactor of the chromatographic type in which the heterogeneous solid phase is capable of acting both as an esterification catalyst and as a means exhibiting preferential adsorption towards one of the reaction products (typically water). The process to which the present invention relates is particularly improved compared with conventional technology owing to the use, as the means for regenerating the catalyst, of a desorbent to which has been added a second compound which, by chemical reaction, completes the removal of the adsorbed water.

TECHNICAL FIELD OF THE INVENTION

Esterification reactions are limited by a chemical equilibrium and therefore techniques for the industrial preparation of an ester involve two consecutive steps. The first is the reaction itself, which finishes when the conditions of equilibrium have been reached. A second step is therefore necessary in order to separate the products of interest from the mixture containing products and reagents. The disadvantages of that technique are of an economic nature because, apart from the energy costs involved in the separation operations, it involves the use of different reactors and separators.

A more advantageous technique resides in combining those two steps in a single reaction and separation apparatus. This can be carried out either in a continuous or in a semi-continuous unit, using various separating techniques, such as: evaporation, distillation, chromatography or the use of membranes. U.S. Pat. No. 4,435,595 describes, for example, the use of reactive distillation to produce high-purity methyl acetate, by esterifying methanol and acetic acid. The process provides for the use of acetic acid and methanol which flow in counter-current through a single reactive distillation column in the presence of an acid catalyst (for example sulphuric acid).

The acetic acid, in addition to being a reagent, also acts as an extracting agent for the non-reacted methanol and for the water which has been produced. Therefore, the methyl acetate is separated continuously from the acetic acid and removed from the top of the column.

Using reactive distillation, it is therefore possible to take the reaction beyond the equilibrium conversion value. One of the major disadvantages of that technique is the cost of the reactive distillation column. Owing to the fact that sulphuric acid is used as the reaction catalyst, the column has to be constructed using a suitable material that is not subject to corrosive phenomena, and therefore using expensive materials.

Reactive chromatography is described as a technique employing a chromatographic system which is used both to convert one or more components and, at the same time, to separate one or more of the products which have been formed. Sardin and Villermaux (Nuov. J. Chim. 1979, 3, 255) have proposed the reaction of acetic acid and ethyl alcohol to form ethyl acetate and water and the simultaneous separation of the products in a fixed-bed chromatographic reactor operating in discontinuous mode. The solid contained in the fixed bed is a mixture of activated alumina for effecting separation and cationic resins in acid form for catalysing the esterification reaction. The ethyl acetate produced is not adsorbed by the bed, while the water is; this enables the two products to be separated. The system operates in a pulsed manner and exhibits a conversion greater than that which can be produced at equilibrium.

Mazzotti et al. (Chem. Eng. Sci. 1996, 51 1827 and Ind. Eng. Chem. Res. 1997, 36,3) propose the use of ion exchange resins in acid form in a discontinuous chromatographic reactor for the esterification reaction between acetic acid and ethyl alcohol. Apart from catalytic capabilities, the resins also exhibit selective adsorption properties suitable for promoting the separation of the reaction products. Analogously (U.S. Pat. No. 5,405,992) a process is proposed which uses a S.M.B.R. (Simulated Moving Bed Reactor) for esterification between an alcohol and a carboxylic acid. The proposed system acts as a catalyst for esterification and as an adsorbent for only one of the products. The adsorbed compound is subsequently regenerated by means of a suitable desorbent. The system is filled with macroreticular ion-exchange resin in acid form, which is efficient both as a catalyst and as a selective adsorbent for water.

That technology is limited by the regeneration stage and by the subsequent separation operation for recovering the desorbent. It has been ascertained several times that the enormous amount of desorbent, which is indispensable for returning the resin bed to the initial conditions (that is to say, in order to desorb all of the water) makes the process economically disadvantageous.

DESCRIPTION OF THE INVENTION

The invention forming the subject of the present patent resides in using for the bed-regeneration stage, not a desorbent capable of removing the water by physical action, as in all the previous applications of reactive chromatography, but a desorbent to which has been added a second compound, known as the reactive desorbent, which removes the water not by physical action but by chemical reaction. The invention to which the present patent relates concerns an economically advantageous process for effecting esterification reactions (especially for the production of acetic esters) which have a composition at equilibrium which is distinctly unfavourable to the production of the ester. A clear example of this process is the synthesis of glycerol triacetate (triacetin) where three molecules of acetic acid are reacted with one molecule of glycerin using the acetic acid as the solvent; this reaction is normally carried out with heterogeneous catalysis on strong cationic macroreticular resins in acid form which act both as a catalyst for the esterification reaction and as an adsorbent for the water produced in the reaction.

In more detail, the esterification process constituting the subject of the present invention comprises the following steps:

(a) effecting the esterification reaction between an alcohol and a carboxylic acid in a chromatographic reactor filled with a substance capable of catalysing the esterification reaction while at the same time adsorbing the water produced;

(b) recovery of the non-adsorbed phase constituted mainly by the ester produced;

(c) removal of the water adsorbed by the catalyst by washing with a desorbent mixture composed of at least one organic solvent in combination with an organic compound capable of reacting with the water.

The non-adsorbed phase recovered in point (b) is then purified by distillation. The alcohol and the carboxylic acid are normally added at the top of the chromatographic reactor without the need for other solvents. In this connection, it should be emphasised that the methods used to carry out steps (a) and (b) are well known in the art and therefore do not require detailed explanation; they are described, for example, in: U.S. Pat. Nos. 4,435,595; 5,405,992; Sardin et al. Estérification catalysée par une resine échangeuse de cation dans un reacteur chromatographique, Nou-veau Journal de chimie, vol. 3, no. 4-1979, 255–261; Mazzotti et al., A continuous chromatographic reactor: SMBR, Chem. Eng. Science, Vol. 51, no. 10, 1827–1836, 1996; the content of which is to be regarded as an integral part of the present description.

The organic solvent used in point (c) is generally the alcohol and/or organic acid used in the esterification reaction. In the case of carboxylic acids that are soluble under the esterification reaction conditions, the organic solvent is normally the carboxylic acid; alternatively, in the case of carboxylic acids that are insoluble and alcohols that are soluble under the esterification reaction conditions, the organic solvent is the alcohol The process according to the present invention is particularly suitable in reactions for the esterification of carboxylic acids containing from 1 to 18 carbon atoms, preferably from 1 to 12, or mixtures thereof; monocarboxylic, dicarboxylic and tricarboxylic acids can be used for the present purposes; in particular, acetic acid is generally preferred as the monocarboxylic acid whereas citric acid is generally preferred as tricarboxylic acid (normally dissolved in a suitable organic solvent. i.e. acetone, methanol, ethanol or methyl ethyl ketone).

The alcohol used in the process according to the present invention is generally an esterifiable alcohol or glycol selected from methanol, ethanol, propanol, butanol, cyclohexanol, benzyl alcohol, phenol, cresol, ethylene glycol, propylene glycol, glycerin.

In the preferred embodiment of the present invention, the organic compound capable of reacting with water is an anhydride, normally the anhydride corresponding to the carboxylic acid used in the esterification reaction, preferably acetic anhydride. The anhydride reacts with the water adsorbed by the substance capable of catalysing the esterification reaction, thus freeing two molecules of the corresponding acid; if the anhydride corresponding to the carboxylic acid used in the esterification reaction is employed, the acid produced during the desorption stage can be recycled in the subsequent esterification reaction.

In order to improve the efficiency of the entire process, step (a) may also be carried out in the presence of the anhydride used in the desorption step (c); that anhydride is preferably used in an amount of from 0.05 to 0.5 equivalent relative to the alcohol and the carboxylic acid that are used in the esterification reaction. Step (a) is normally carried out at a temperature of from 20 to 160° C., preferably from 40 to 100° C. and at a pressure of from 0 to 5 bar, preferably from 1 to 2 bar Still in the preferred embodiment of the invention, the anhydride constitutes from 1 to 10% by weight of the desorbent mixture, preferably from 4 to 6%; step (c) is also carried out at a temperature of from 20 to 160° C., preferably from 40 to 100° C. and at a pressure of from 0 to 5 bar, preferably from 1 to 2 bar.

The substance capable of catalysing the esterification reaction is generally an ion exchange resin in acid form, such as, for example, the resins Amberlyst 15™ or Bayer K 2641™; the process may also operate either continuously or discontinuously.

In the more advantageous embodiment of the invention, the alcohol is glycerin, the carboxylic acid is acetic acid (the esterification product being preferably triacetin), the desorbent mixture is composed of acetic acid and acetic anhydride, the acetic anhydride being present in an amount such that it constitutes from 4 to 6% by weight, and step (c) is carried out at a temperature of from 40 to 100° C. and at a pressure of from 1 to 2 bar.

As will be readily appreciated, using the present process it is possible to obtain the final ester with an extremely high degree of purity and with a water content that is normally less than 0.05% by weight. In the case of the synthesis of polyesters, such as, for example, triacetin, the desired final product is also substantially free from the corresponding ester secondary products, or mono- and di-acetin, which are eluted from the reactor separately and may optionally be recycled in the esterification process.

Another embodiment of the present invention is a partial esterification reaction between poly-alcohols and/or poly-organic acids in order to obtain an ester having at least one free alcoholic and/or acid group. In this preferred embodiment of the invention, the alcohol may be glycerin whereas the carboxylic acid may be acetic acid, the esterification product being for instance diacetin: the aim of the invention is in this case that of obtaining a diacetin concentration in the mixture leaving the column which is higher than that obtained at the equilibrium (approximately 27%). In this case step (a) may be carried out at a temperature of from 20 to 100° C., preferably from 20 to 50° C. and at a pressure of from 1 to 2 bar; the desorbent mixture may be composed of acetic acid and acetic anhydride, the acetic anhydride being present in an amount such that it constitutes from 4 to 6% by weight; step (c) may be carried out at a temperature of from 20 to 100° C. and at a pressure of from 1 to 2 bar Those and other aspects of the process according to the present invention are demonstrated in the appended Examples which are to be regarded purely as illustrative and non-limiting.

EXAMPLE 1

An esterification reaction is carried out between acetic acid and glycerin in a reactor having a fixed bed of Amberlyst 15™ cationic macroreticular resins in acid form (38 g): the column, having a diameter of 1.4 cm and a length of 46 cm, is thermostated at 80° C.

The aim is to effect a chromatographic reaction and therefore to obtain a triacetin concentration in the mixture leaving the column which is higher than that obtained in the equilibrium conversion (approximately 7%) and at the same time to separate the triacetin from the other reaction products (diacetin, monoacetin and water). The column is initially regenerated with acetic acid, until the water content of the solution leaving the column is identical to that of the acid supplied (in this case the water content is 7.5 parts per thousand). As soon as the reaction mixture composed of acetic acid and glycerin (ratio 4.5/1, that is to say, with an aliquot of acid higher by 50% than the stoichiometric amount) has been supplied, the catalytic activity of the resin promotes the esterification reaction. The water produced during the reaction is captured by the resin, while the ester, which has less affinity for the resin, is partially desorbed and is carried forwards by the flow in the column. Thus, the esterification proceeds beyond the equilibrium conversion, until the limiting reagent, which is initially glycerin and then, when the glycerin has been exhausted, the monoacetin and then the diacetin, has been totally consumed.

The process continues until the water saturates the resin column completely. When saturation is complete, the local composition profile remains constant and the resin exercises a purely catalytic activity.

Figure 1:
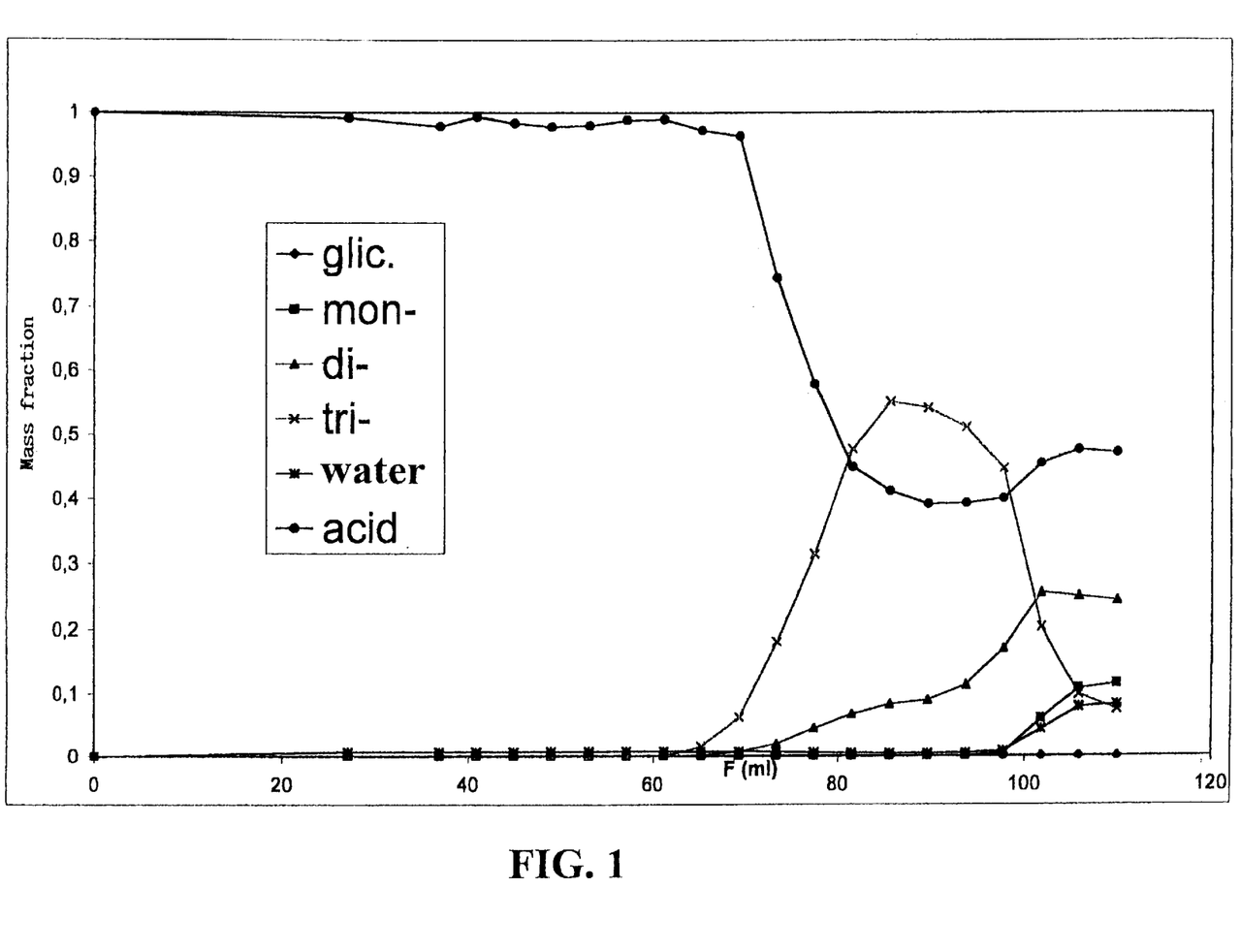
FIG. 1 is a graph illustrating the development over time of the liquid composition at the outlet of the reactor as a function of the volume of the reagents supplied.

FIG. 1 shows the development over time of the liquid composition at the outlet of the reactor as a function of the volume of the reagents supplied. It can be seen that the triacetin is the first to be eluted from the column and its percentage value far exceeds that of the equilibrium conversion. Not far from the elution of the triacetin, however, that of the diacetin can also be seen. It will be appreciated, therefore, that separation of those two products is not optimum and, because our principal aim is to obtain pure triacetin, that objective is reached only partially in this Example. On the other hand, for a good part of the test, there is an outgoing flow containing solely the triacetin and diacetin mixture (in addition to the acetic acid). When the water saturates the resin, the monoacetin, the glycerin and the water are eluted and equilibrium conditions are established.

EXAMPLE 2

In this case the operating conditions are the same as in the previous Example except that acetic acid suitably dried by prolonged contact with anhydrous molecular sieves is used. The residual amount of water in the acid is 2.59 parts per thousand. The acid is used for regeneration until a water content is obtained at the outlet of the column which is comparable to that at the inlet. All the other operating parameters remain unchanged.

Figure 2:
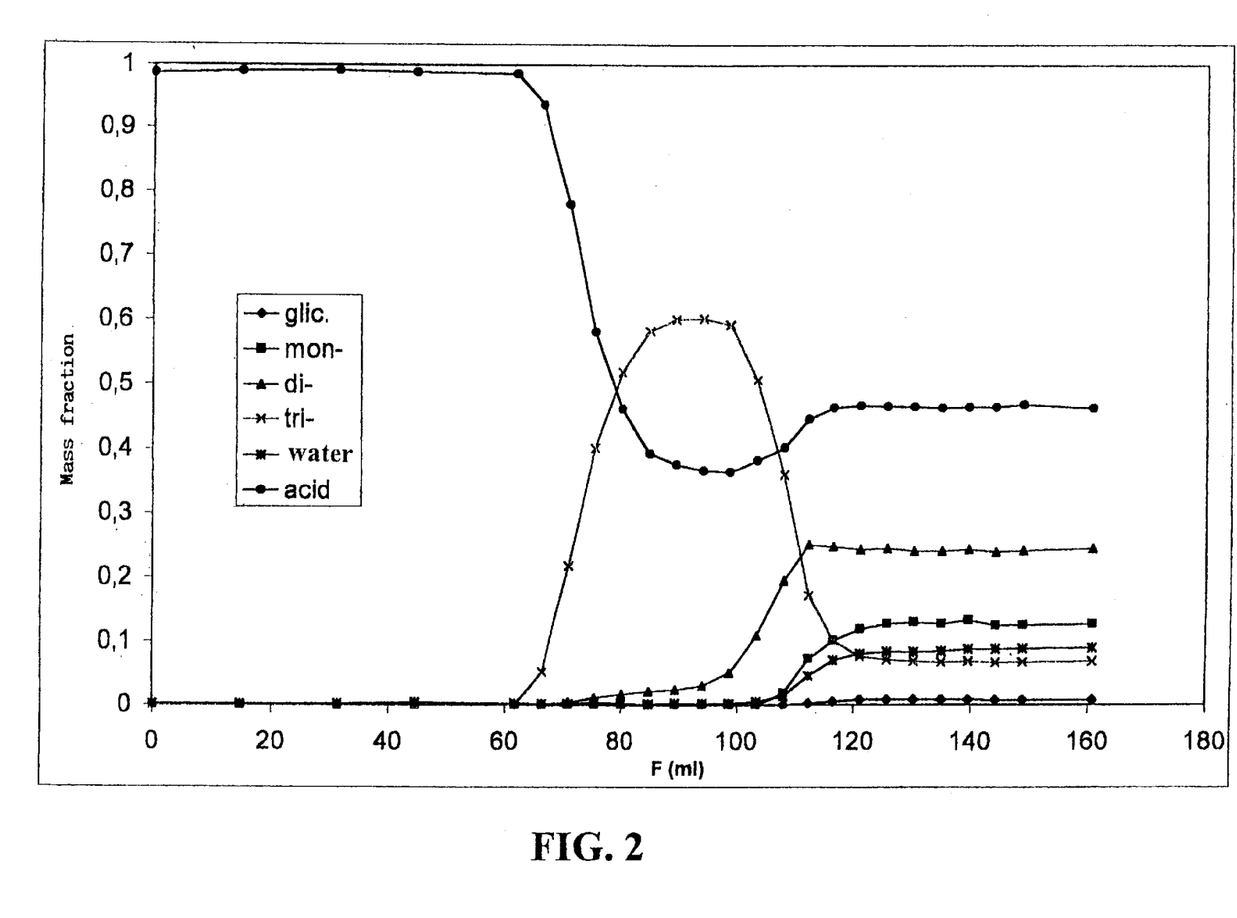
FIG. 2 is a graph illustrating the progress of the individual products leaving the reactor as a function of the volume of the reagents supplied.

FIG. 2 shows the progress of the individual products leaving the reactor as a function of the volume of the reagents supplied. It can be seen that, in this case, the separation of triacetin and diacetin is substantially improved. The diacetin is always eluted fairly quickly (approximately 20 ml after the triacetin) but its percentage value is decidedly low (less than 3%) for a long period and remains almost constant until the triacetin has reached its maximum.

All this confirms that the water content initially present in the resin is responsible for the good functioning of the process and, above all, plays a determining role in the separation of triacetin and diacetin. This means that very high resin-drying levels must be achieved in the regeneration stage, with a consequent increase in the amounts of desorbent, which will thus involve costs for the recovery thereof.

EXAMPLE 3

In this case, the operation is again carried out with an amount of resin (Amberlyst 15) identical to that of Example 1 (38 g), but the resin is regenerated with a previously prepared mixture of acetic acid/acetic anhydride (5% by weight of anhydride).

At the end of the regeneration stage and after checking that the water content of the solution being discharged is less than 5 parts per ten thousand, that is to say, is comparable to the value of the water present in the regenerating mixture, a mixture composed of acetic acid/acetic anhydride/glycerin in the following molar ratio (4.25/0.13/1) is introduced.

Figure 3:
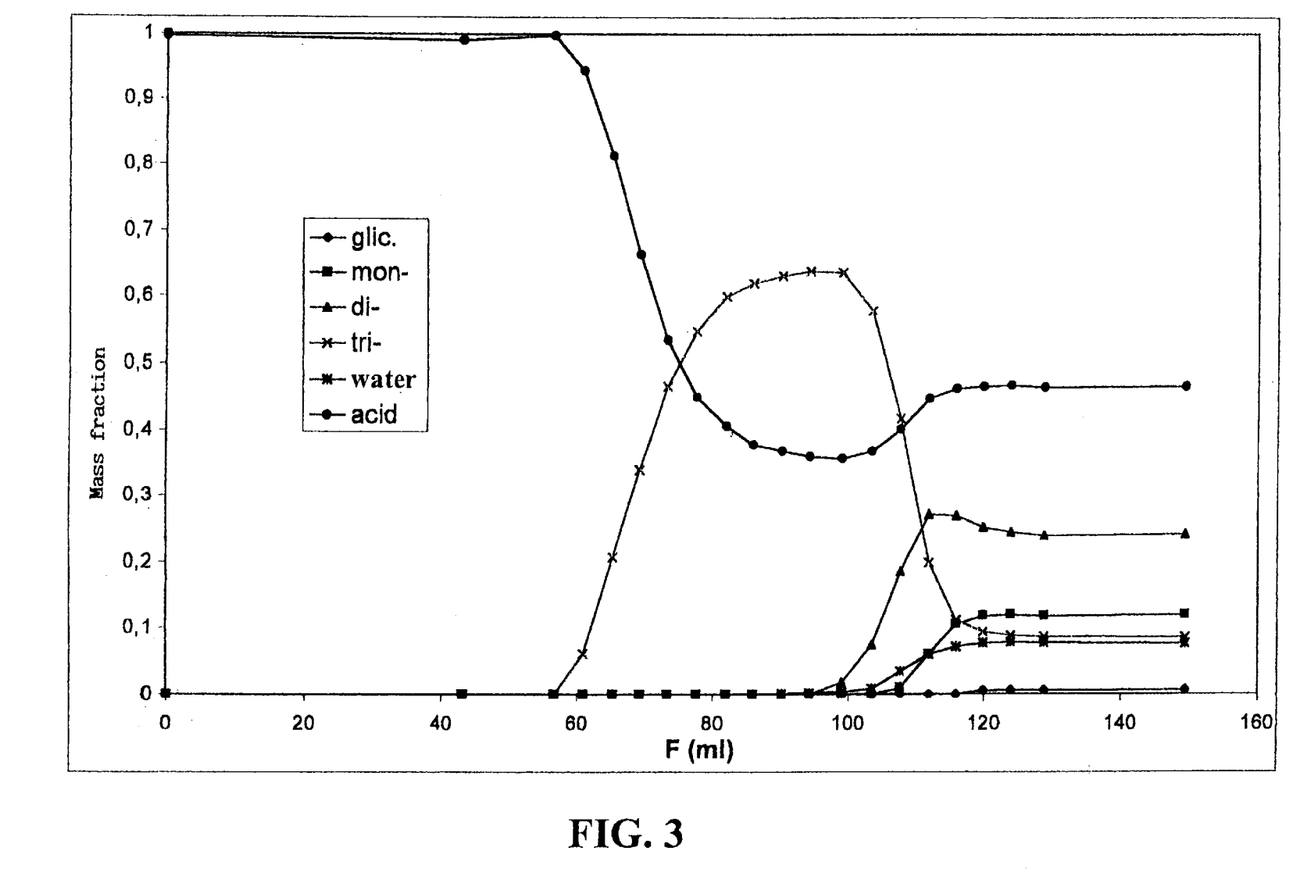
FIG. 3 is a graph illustrating the improvement of the separation of triacetin and diacetin.

As will be appreciated from FIG. 3, the separation of triacetin and diacetin is decidedly improved compared with all of the previous cases. After the triacetin has emerged there is (for approximately 40 ml of discharged solution) only triacetin and acetic acid. After this interval, the diacetin, the monoacetin, the glycerin and the water emerge close together. All this demonstrates that, by operating under these conditions, the chromatographic reactor functions in an optimum manner both from the catalytic point of view and from the point of view of separation. As long as it is not completely saturated, the resin is able to adsorb all the water that is formed in the course of the reaction and is able to move the esterification towards the production of triacetin only.

EXAMPLE 4

Desorption With Glacial Acetic Acid

At the end of the reaction, as soon as equilibrium conditions have been established, all of the water adsorbed on the resins must be desorbed from the column by means of a suitable desorbent.

For reasons which will be readily appreciated, it is preferable for the desorbent to be one of the reagents of the reaction in question. It is impossible to use glycerin for this purpose owing to its high viscosity and therefore the regeneration process was initially carried out with glacial acetic acid.

The operation is carried out at 80° C. with an acid flow rate of 0.5 ml/min.

Figure 4:
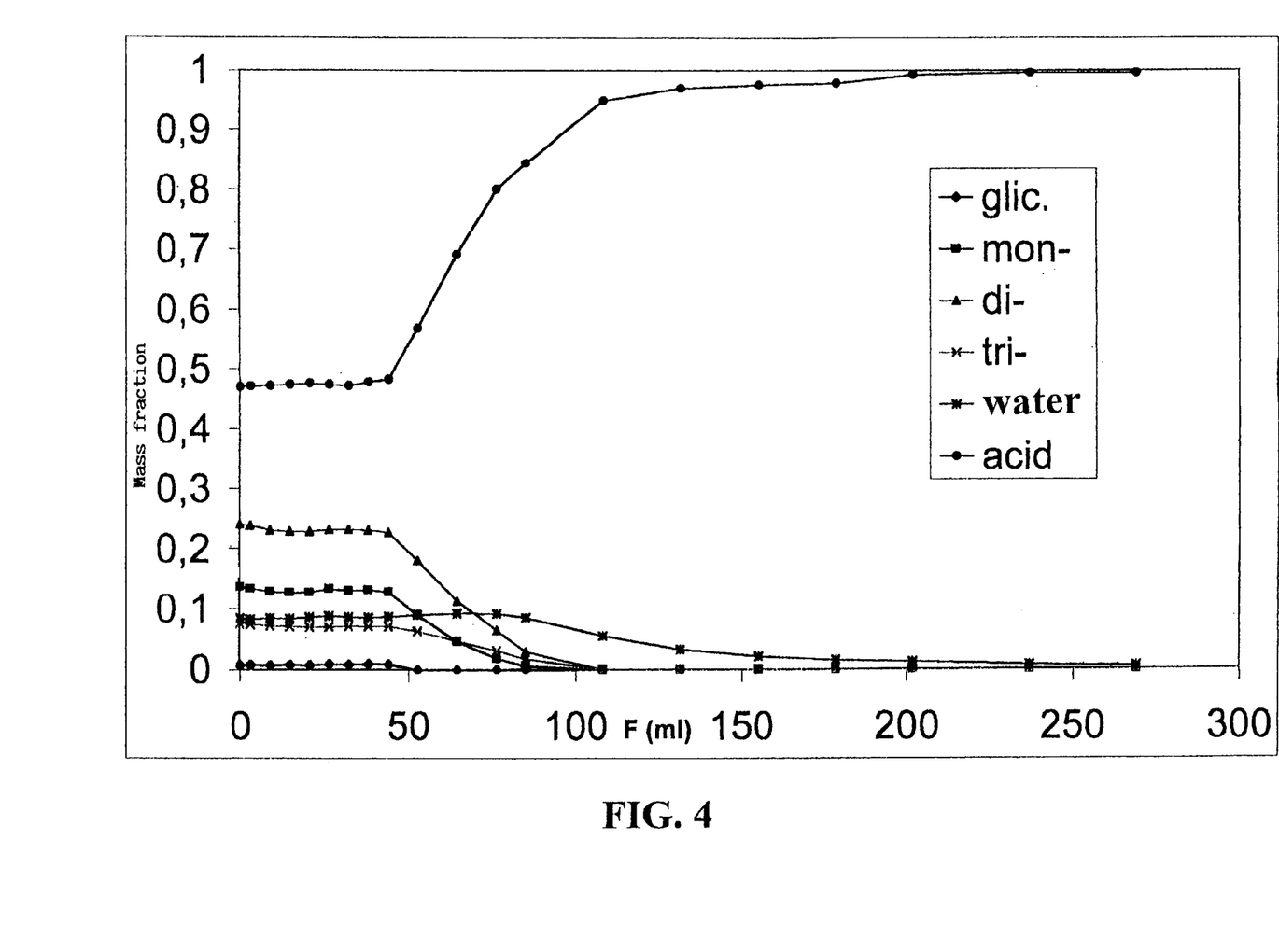
FIG. 4 is a graph illustrating the progress of all of the products desorbed from the column as a function of the volume of desorbent used.

FIG. 4 shows the progress of all the products desorbed from the column as a function of the volume of desorbent used.

It can be seen that the glycerin, the triacetin, the diacetin and the monoacetin are rapidly eluted from the column, while the water, owing to its strong affinity for the resin, is difficult to desorb.

Even after 250 ml of acetic acid have been introduced, the water content at the outlet is 8 parts per thousand, which is markedly higher than that initially present in the acid (2 parts per thousand). It will also be observed that, after 200 ml of acid have been introduced, the water value is still 1.2%.

It will also be appreciated that it will never be possible to descend to a water value in the discharged mixture lower than that present in the acid supplied for desorption.

EXAMPLE 5

Desorption With Acetic Acid/acetic Anhydride

In this case the regeneration process was carried out with an acetic acid/acetic anhydride mixture (5% by weight of anhydride), still at 80° C. and with a supply rate of 0.5 ml/min.

Figure 5:
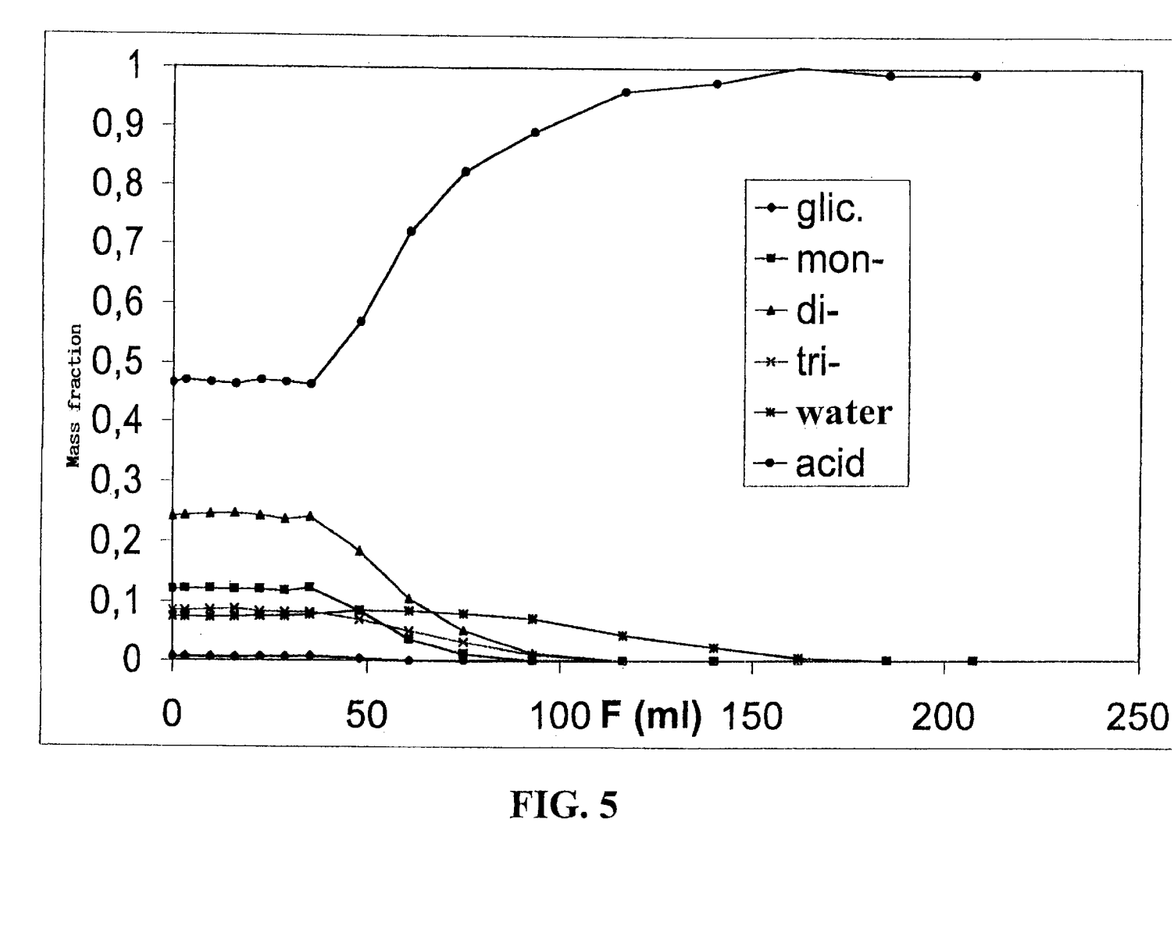
FIG. 5 is a grpah illustrating the rapid rate of desorption of monacetin, diacetin and triacetin.

As can be seen in FIG. 5, the rate of desorption of monoacetin, diacetin and triacetin is rapid, as in the previous case. However, the water is desorbed with a substantially smaller volume of desorbent than in the previous case and, above all, it is possible to arrive at extremely low percentages of water at the outlet of the column. In fact, after 160 ml of desorbent have been introduced, the water value in the discharged mixture is equal to 5 parts per thousand and, after 180 ml have been introduced, that value is lower than 2 parts per ten thousand.

It can therefore be affirmed that, at this point, the resin is completely free from the water formed during esterification and is therefore suitable again for a fresh reaction cycle.

Furthermore, the amounts of desorbent used are much lower and therefore the costs involved in its recovery are also lower. To these, however, is added the higher cost of acetic anhydride compared with that of acetic acid.

EXAMPLE 6

An esterification reaction is carried out between acetic acid and glycerin in a reactor having a fixed bed of Bayer K 2641™ cationic macroreticular resins in acid form (430 g): the column, having a diameter of 3.5 cm and a length of 100 cm, is thermostated at 40° C.

The aim is to effect a partial reaction and therefore to obtain a diacetin concentration in the mixture leaving the column which is higher than that obtained at the equilibrium (approximately 27%) and at the same time to separate the diacetin from the other reaction products (triacetin, monoacetin, glycerin and water).

The column is initially regenerated with acetic acid, until the water content of the solution leaving the column is identical to that of the acid supplied (in this case the water content is 7.5 parts per thousand). As soon as the reaction mixture composed of acetic acid and glycerin and acetic anhydride and water (ratio 0.97/1.0/0.07/0, that is to say, with an aliquot of acid lower than the stoichiometric amount for the complete esterification) has been supplied, the catalytic activity of the resin promotes the esterification reaction. The water produced during the reaction is captured by the resin, while the ester, which has less affinity for the resin, is partially desorbed and is carried forwards by the flow in the column.

Thus, the esterification proceeds beyond the equilibrium conversion, until the limiting reagent, which is initially glycerin and then, when the glycerin has been exhausted, the monoacetin, has been mainly consumed.

Figure 6:
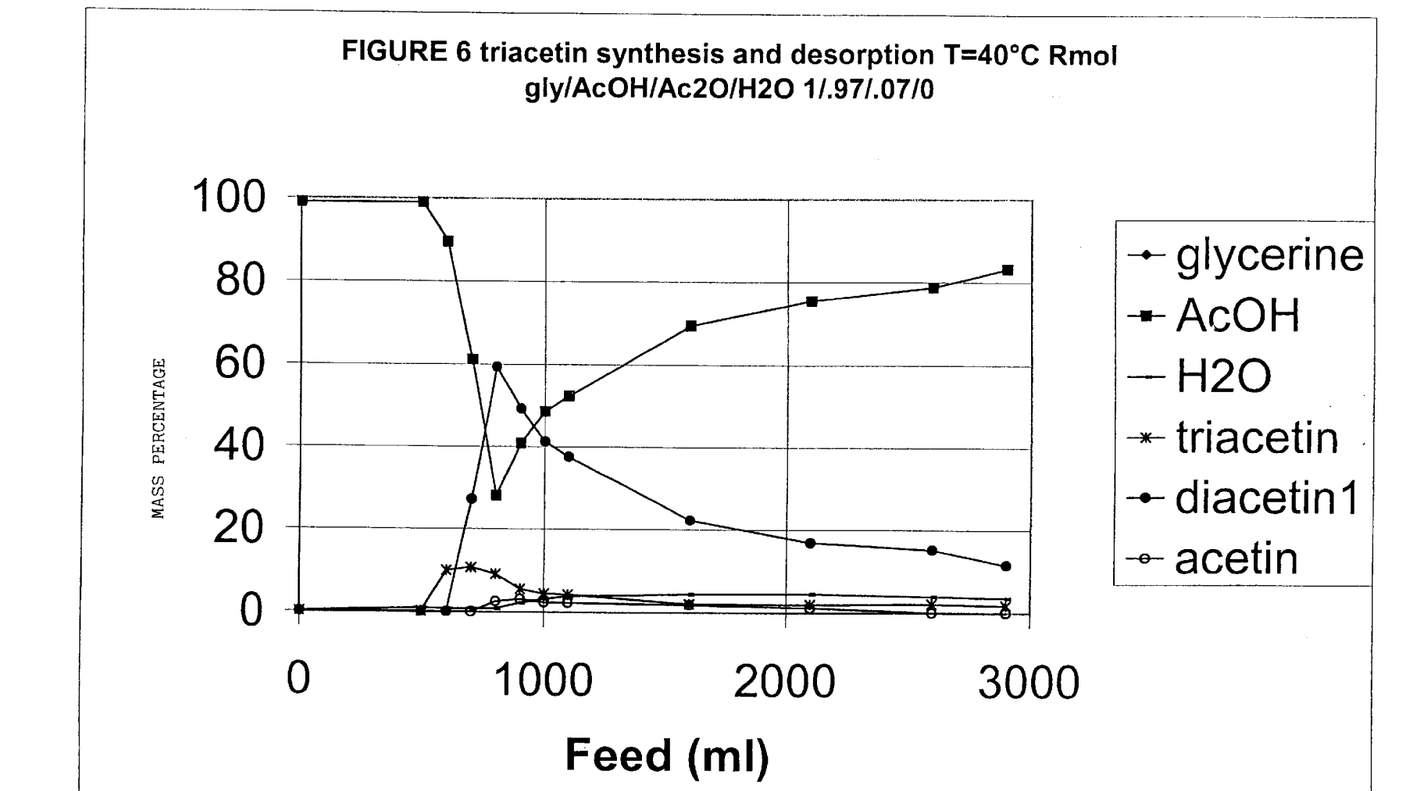
FIG. 6 is a graph illustrating the development over time of the liquid composition at the outlet of the reactor as a function of the volume of the reagents supplied.

FIG. 6 shows the development over time of the liquid composition at the outlet of the reactor as a function of the volume of the reagents supplied. It can be seen that the triacetin is the first product to be eluted from the column. Not far from the elution of the triacetin, however, that of the diacetin can also be seen. For a part of the test, there is an outgoing flow containing mainly the diacetin mixture with lower amount of triacetin monoacetin and glycerin (in addition to the acetic acid).

The operation is carried out with a flow rate of 270 ml/h t the end of the reaction, before the equilibrium conditions have been established, all of the water adsorbed on the resin must be desorbed from the column by means of a suitable desorbent.

In this case the regeneration process was carried out with an acetic acid/acetic anhydride mixture (5% by weight of anhydride), still at 80° C. and with a supply rate of 270 ml/h.

As can be seen in FIG. 6, the rate of desorption of monoacetin, and triacetin is rapid, that of diacetin is not so rapid due to the medium affinity of the diester respect the resin and also for the high percentage.

EXAMPLE 7

An esterification reaction is carried out between acetic acid and glycerin in a reactor having a fixed bed of Bayer K 2641™ cationic macroreticular resin in acid form as in example 6, is thermostated at 30° C.

The aim is to effect a partial reaction and therefore to obtain a diacetin concentration in the mixture leaving the column which is higher than that obtained at the equilibrium (approximately 27%) and at the same time to separate the diacetin from the other reaction products (triacetin, monoacetin, glycerin and water).

The column is initially regenerated with acetic acid, until the water content of the solution leaving the column is identical to that of the acid supplied (in this case the water content is 7.5 parts per thousand). As soon as the reaction mixture composed of acetic acid and glycerin and acetic anhydride and water (ratio 0/1.0/0/0, that is to say, with an aliquot of acid lower than the stoichiometric amount for the complete esterification) has been supplied, the catalytic activity of the resin promotes the esterification reaction.

Thus, the esterification proceeds beyond the equilibrium conversion, until the limiting reagent, which is initially glycerin and then, when the glycerin has been exhausted, the monoacetin, has been mainly consumed.

Figure 7:
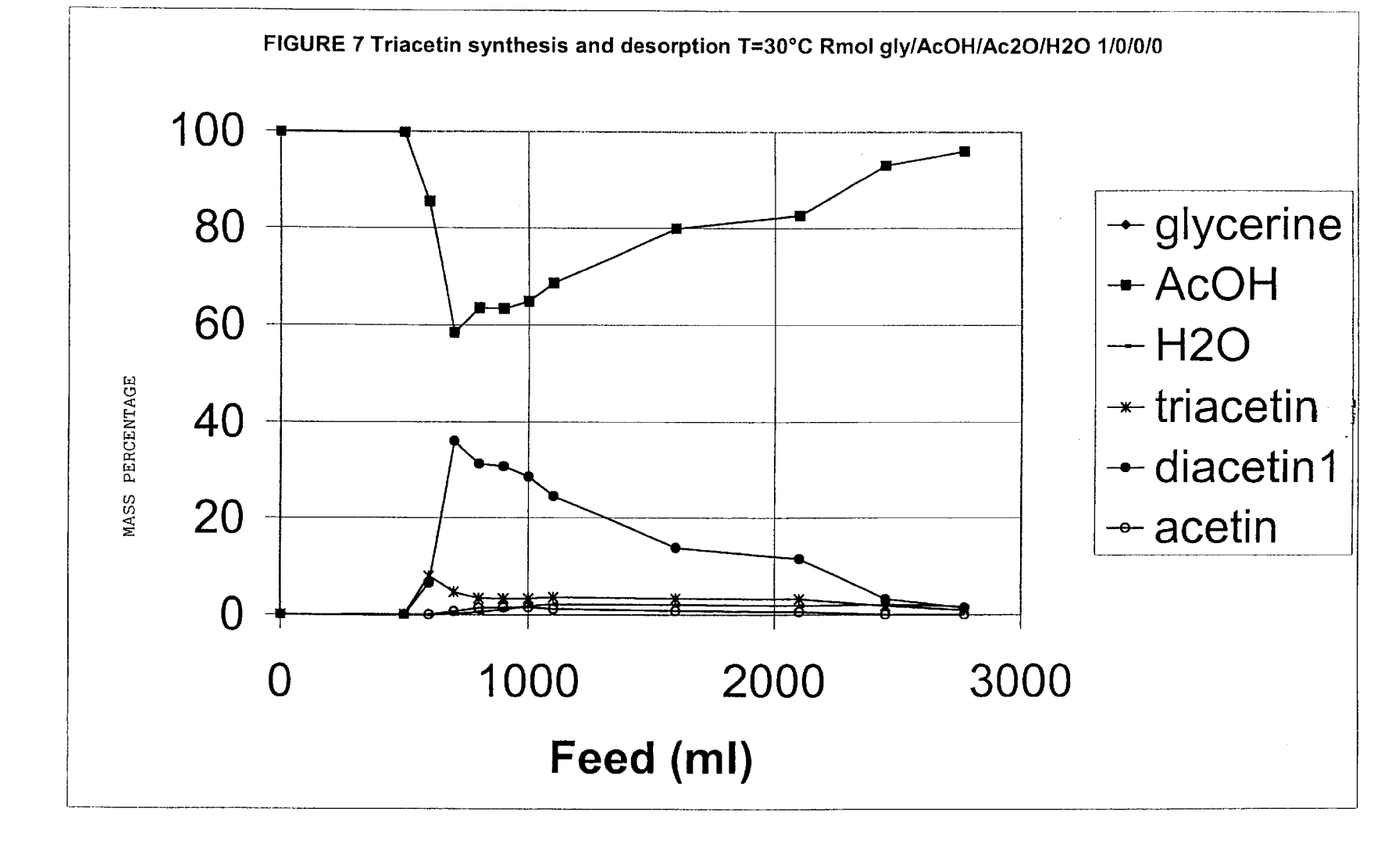
FIG. 7 is a graph illustrating the development over time of the liquid composition at the outlet of the reactor as a function of the volume of the reagents supplied.

FIG. 7 shows the development over time of the liquid composition at the outlet of the reactor as a function of the volume of the reagents supplied. It can be seen that the triacetin is the first to be eluted from the column. Not far from the elution of the triacetin, however, that of the diacetin can also be seen. For a part of the test, there is an outgoing flow containing mainly the diacetin mixture with lower amount of triacetin monoacetin and glycerin (in addition to the acetic acid). The operation is carried out with a flow rate of 270 ml/h At the end of the reaction, before the equilibrium conditions have been established, all of the water adsorbed on the resin must be desorbed from the column by means of a suitable desorbent.

In this case the regeneration process was carried out with an acetic acid/acetic anhydride mixture (5% by weight of anhydride), still at 80° C. and with a supply rate of 270 ml/h.

As can be seen in FIG. 7, the rate of desorption of monoacetin, and triacetin is rapid, that of diacetin is not so rapid due to the medium affinity of the diester respect the resin and also for the high percentage.

Legend

The following abbreviations have been adopted in FIGS. 1 to 5:

glyc=glycerin mon-=monoacetin di-=diacetin tri-=triacetin acid=acetic acid

What is claimed is:

1. An esterification process in a chromatographic reactor comprising the following steps:
   (a) effecting the esterification reaction between an alcohol and a carboxylic acid in a chromatographic reactor filled with a substance capable of catalysing the esterification reaction while at the same time adsorbing the water produced;

(b) recovery of the non-adsorbed phase;

(c) removal of the adsorbed water by washing with a desorbent mixture composed of at least one organic solvent in combination with an anhydride.

2. A process according to claim 1, wherein said at least one organic solvent mentioned in point (c) is the alcohol and/or organic acid used in the esterification reaction.

3. A process according to claim 1, wherein said alcohol is an esterifiable alcohol or glycol selected from methanol, ethanol, propanol, butanol, cyclohexanol, benzyl alcohol, phenol, cresol, ethylene glycol, propylene glycol, glycerin.

4. A process according to claim 1, wherein said carboxylic acid is a monocarboxylic, dicarboxylic or tricarboxylic acid containing from 1 to 18 carbon atoms, preferably from 1 to 12, or mixtures thereof.

5. A process according to claim 1, wherein said carboxylic acid is acetic acid.

6. A process according to claim 1, wherein said carboxylic acid is citric acid.

7. A process according to claim 6, wherein citric acid is dissolved in a suitable organic solvent, preferably acetone, methanol, ethanol or methyl ethyl ketone.

8. A process according to claim 1, wherein said anhydride constitutes from 1 to 10% by weight.

9. A process according to claim 1, wherein said anhydride constitutes from 4 to 6%, of the desorbent mixture.

10. A process according to claim 1, wherein step (a) is carried out in the presence of an anhydride.

11. A process according to claim 10, wherein said anhydride is used in an amount of from 0.05 to 0.5 equivalent relative to the alcohol and the carboxylic acid that are used in the esterification reaction.

12. A process as in any one of claim 8, 9, or 10, wherein said anhydride is the anhydride corresponding to the carboxylic acid used in the esterification reaction.

13. A process according to claim 12, wherein said anhydride is acetic anhydride.

14. A process according to claim 1, wherein said desorbent mixture is constituted by the carboxylic acid used in the esterification reaction and by the corresponding anhydride.

15. A process according to claim 1, wherein said desorbent mixture is constituted by the alcohol used in the esterification reaction and by the anhydride corresponding to the carboxylic acid used in that reaction.

16. A process according to claim 1, wherein step (c) is carried out at a temperature of from 20 to 160° C.

17. A process according to claim 1, wherein step (c) is carried out at a temperature of from 40 to 100° C.

18. A process according to claim 1, wherein step (c) is carried out at a pressure of from 0 to 5 bar.

19. A process according to claim 1, wherein step (c) is carried out at a pressure of from 1 to 2 bar.

20. A process according to claim 1, wherein said substance capable of catalysing the esterification reaction is an ion exchange resin in acid form.

21. A process according to claim 1, operating continuously or discontinuously.

22. A process according to claim 1, wherein said alcohol and wherein said carboxylic acid used in step (a) are glycerin and acetic acid, respectively; and in that step (c) is carried out at a temperature of from 40 to 100° C. and at a pressure of from 1 to 2 bar, and in that the desorbent mixture is composed of acetic acid and acetic anhydride, the acetic anhydride being present in an amount of from 4 to 6% by weight.

* * * * *

UNITED STATES PATENT AND TRADEMARK OFFICE
CERTIFICATE OF CORRECTION

PATENT NO. : 6,586,609 B1
DATED : July 1, 2003
INVENTOR(S) : Roberto Ruggieri et al.

It is certified that error appears in the above-identified patent and that said Letters Patent is hereby corrected as shown below:

<u>Title page,</u>
Item [73], Assignee, please replace "La Chemical SpA, Biella (IT)" with
-- La Chemial SpA, Biella (IT) --.

Signed and Sealed this

Ninth Day of September, 2003

JAMES E. ROGAN
*Director of the United States Patent and Trademark Office*